(12) United States Patent
Roussev et al.

(10) Patent No.: US 9,109,881 B2
(45) Date of Patent: Aug. 18, 2015

(54) PRISM COUPLING METHODS WITH IMPROVED MODE SPECTRUM CONTRAST FOR DOUBLE ION-EXCHANGED GLASS

(71) Applicant: Corning Incorporated, Corning, NY (US)

(72) Inventors: Rostislav Vatchev Roussev, Painted Post, NY (US); Emily Elizabeth Young, Erin, NY (US)

(73) Assignee: Corning Incorporated, Corning, NY (US)

( * ) Notice: Subject to any disclaimer, the term of this patent is extended or adjusted under 35 U.S.C. 154(b) by 0 days.

(21) Appl. No.: 14/289,056

(22) Filed: May 28, 2014

(65) Prior Publication Data
US 2014/0368808 A1    Dec. 18, 2014

Related U.S. Application Data

(60) Provisional application No. 61/937,726, filed on Feb. 10, 2014, provisional application No. 61/860,560, filed on Jul. 31, 2013, provisional application No. 61/835,823, filed on Jun. 17, 2013.

(51) Int. Cl.
*G01B 11/16* (2006.01)
*G01N 21/00* (2006.01)
*G01L 1/24* (2006.01)

(52) U.S. Cl.
CPC ............... *G01B 11/16* (2013.01); *G01L 1/241* (2013.01); *G01N 21/00* (2013.01)

(58) Field of Classification Search
CPC ........................................................ G01B 11/16
USPC ........................................................... 356/32
See application file for complete search history.

(56) References Cited

U.S. PATENT DOCUMENTS

| 3,308,394 | A | 3/1967 | Snitzer et al. | |
|---|---|---|---|---|
| 8,957,374 | B2 * | 2/2015 | Liu et al. | 250/338.1 |
| 2014/0092377 | A1 * | 4/2014 | Liu et al. | 356/51 |

* cited by examiner

*Primary Examiner* — Roy M Punnoose
(74) *Attorney, Agent, or Firm* — Payal A. Patel

(57) ABSTRACT

Methods of capturing improved-contrast mode spectra of a double ion-exchanged (DIOX) glass sample using prism coupling of index $n_p$. The DIOX glass sample has a refractive index profile with a first region adjacent the surface that satisfies $$0.0005 \leq \left|\frac{\lambda}{n}\frac{dn}{dx}\right| \leq 0.0009,$$

where $\lambda$ is a wavelength of measuring light. The prism-sample interface includes an interfacing liquid of index $n_f$ that differs from $n_p$ by no more than 0.03, and that can exceed $n_p$. The mode spectra have a contrast that is higher than that obtained by conventional prism coupling by using gradient illumination or partially blocked illumination that reduces the amount of background reflected light from the coupling prism. The improved-contrast mode spectra can be processed using conventional means to determine at least one stress characteristic of the DIOX glass sample.

21 Claims, 14 Drawing Sheets

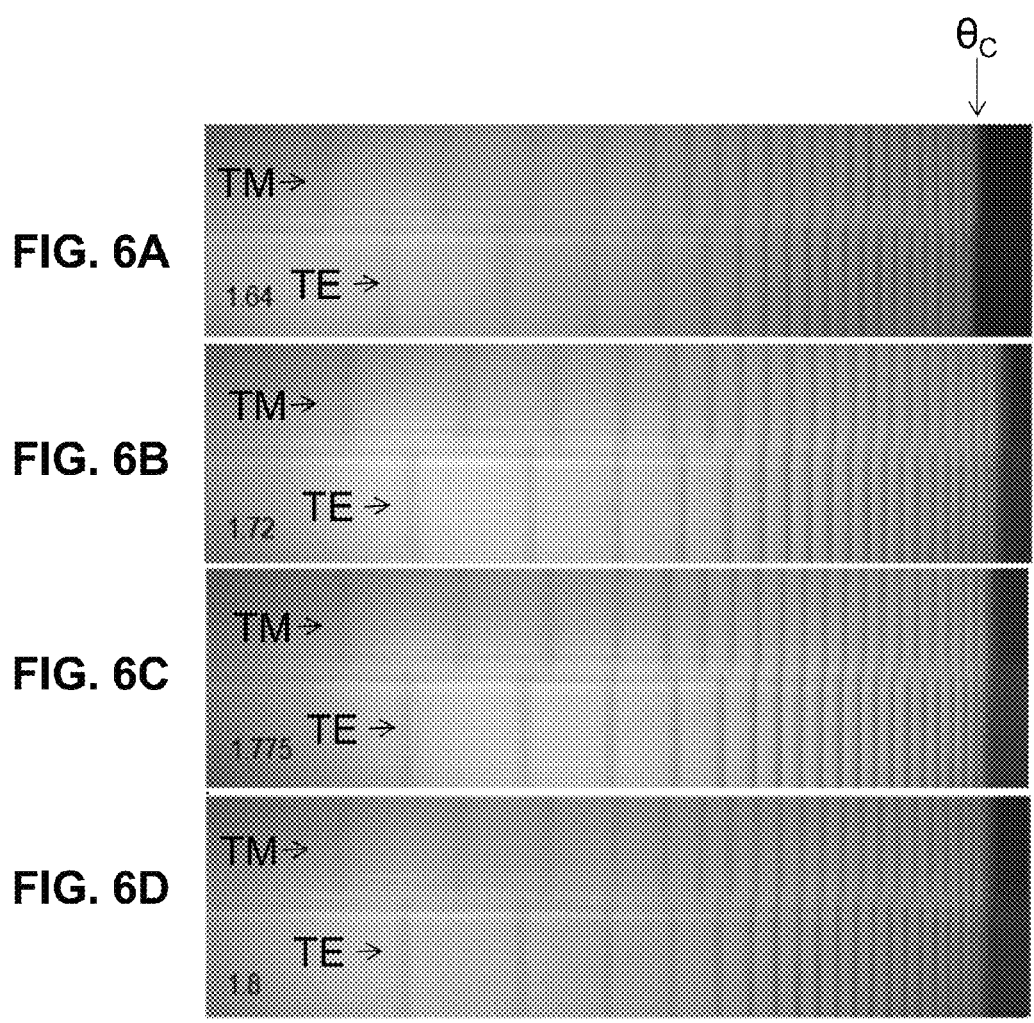

US 9,109,881 B2

PRISM COUPLING METHODS WITH IMPROVED MODE SPECTRUM CONTRAST FOR DOUBLE ION-EXCHANGED GLASS

This application claims the benefit of priority under 35 U.S.C. §119 of U.S. Provisional Application Ser. No. 61/835,823, filed on Jun. 17, 2013, U.S. Provisional Application Ser. No. 61/860,560, filed on Jul. 31, 2013, and U.S. Provisional Application Ser. No. 61/937,726, filed on Feb. 10, 2014, the contents of which are relied upon and incorporated herein by reference in their entirety.

FIELD

The present disclosure relates to measuring stress characteristics of ion-exchanged glass using prism coupling, and in particular relates to methods of obtaining improved mode spectrum contrast when measuring double ion-exchanged glass using prism coupling to determine at least one stress characteristic in the double ion-exchanged glass.

BACKGROUND

Certain types of glasses and glass-ceramics can be chemically strengthened by an ion exchange process that may change the surface refractive index of the material. The strengthening is due to the formation of a near-surface compression layer that usually creates birefringence. The birefringence in turn corresponds to a change in refractive index profile in the glass.

There is increasing commercial interest in chemically strengthened glasses with anti-microbial (AM) surface properties. Such glasses can be fabricated using a double ion-exchange process (DIOX) wherein first IOX is performed for strengthening wherein a larger alkali ion such as $K^+$ exchanges for a smaller alkali ion such as $Na^+$ or $Li^+$ in the original base glass. This gives a refractive-index profile similar to that shown in the plot of refractive index n vs. depth x shown in FIG. 1A. The first IOX is followed by a second IOX using an anti-microbial element, such as $Ag^+$. This gives rise to a refractive index profile similar to that shown in FIG. 1B, wherein the profile contains a region R1 that has a relatively steep slope and is relatively shallow (e.g., just a few microns in depth x), along with a deeper region R2 of less slope but greater depth. In FIGS. 1A and 1B, the prism refractive index is denoted $n_p$, the interfacing fluid (which may also be referred as oil, immersion fluid or index-matching fluid) is denoted $n_f$, the base substrate refractive index is denoted $n_s$, and the elevated substrate surface refractive index is $n_0$.

With the increased use of chemically strengthened glasses in such products as smart phones, computer screens and flat-panel televisions, there is an increasing need for nondestructive, high-throughput measurements of the surface stress in such glasses for quality control during manufacturing.

Unfortunately, conventional stress profile measurement techniques that employ prism coupling that work for the profile associated with FIG. 1A are inadequate for characterizing the stress profile associated with FIG. 1B because they cannot resolve the TM and TE mode spectra with adequate contrast.

SUMMARY

An aspect of the disclosure a method of characterizing a compressive stress of a double ion-exchanged (DIOX) glass sample having a surface and a base refractive index $n_s$, comprising: wetting either a coupling surface of a coupling prism of refractive index $n_p$ or the DIOX sample surface with an interfacing fluid having a refractive index $n_f$; interfacing the coupling prism to the surface of the DIOX sample to define a prism-sample interface having input and output ends, with the interfacing fluid residing between the coupling prism and the DIOX sample surface, wherein $n_f$ differs from $n_p$ by no more than 0.03, and wherein the sample has a refractive index profile with a region adjacent the surface that satisfies $$0.0004 \leq \left| \frac{\lambda}{n} \frac{dn}{dx} \right| \leq 0.0013,$$

where $\lambda$ is a wavelength of measuring light; illuminating the prism-sample interface with the measurement light, wherein the measurement light has an intensity gradient that increases in the direction from the input to the output end of the prism-sample interface; digitally capturing TE and TM mode spectra reflected from the prism-sample interface; and processing the TE and TM mode spectra to determine the compressive stress of the DIOX sample.

Another aspect of the disclosure is a method of characterizing a compressive stress of DIOX glass sample having a surface and a base refractive index $n_s$. The method includes: wetting either a coupling surface of a coupling prism of refractive index $n_p$ or the DIOX sample surface with an interfacing fluid having a refractive index $n_f$; interfacing the coupling prism to the surface of the DIOX sample to define a prism-sample interface having input and output ends, with the interfacing fluid residing between the coupling prism and the DIOX sample surface, wherein $n_f$ differs from $n_p$ by no more than 0.03, and wherein the sample has a refractive index profile with a region adjacent the surface that satisfies $$0.0004 \leq \left| \frac{\lambda}{n} \frac{dn}{dx} \right| \leq 0.0013,$$

where $\lambda$ is a wavelength of measuring light; illuminating the prism-sample interface with the measurement light, wherein a portion of the measurement light at the input end of the prism-sample interface is either partially or completely blocked; digitally capturing TE and TM mode spectra reflected from the prism-sample interface; and processing the TE and TM mode spectra to determine the compressive stress of the DIOX sample.

Additional features and advantages are set forth in the Detailed Description that follows and in part will be readily apparent to those skilled in the art from the description or recognized by practicing the embodiments as described in the written description and claims thereof, as well as the appended drawings. It is to be understood that both the foregoing general description and the following Detailed Description are merely exemplary and are intended to provide an overview or framework for understanding the nature and character of the claims.

BRIEF DESCRIPTION OF THE DRAWINGS

The accompanying drawings are included to provide a further understanding, and are incorporated into and constitute a part of this specification. The drawings illustrate one or more embodiment(s) and together with the Detailed Description serve to explain the principles and operation of the various embodiments. As such, the disclosure will become more fully understood from the following Detailed Description, taken in conjunction with the accompanying Figures, in which:

FIGS. 6A through 6D are captured images of TE and TM mode spectra images of the above-described DIOX sample as obtained using a commercial version of the prism-coupling system of FIG. 2A, for interfacing fluids in the form of oils having refractive indices $n_f$ of 1.64, 1.72, 1.775 and 1.8, respectively;

FIGS. 13A and 13B are captured TM and TE mode spectra, wherein FIG. 13A is a baseline taken using prior-art uniform illumination while FIG. 13B was taken using gradient illumination.

Any coordinates or axes shown in the Figures are for the sake of reference and are not intended to be limiting as to direction or orientation.

DETAILED DESCRIPTION

Reference is now made in detail to various embodiments of the disclosure, examples of which are illustrated in the accompanying drawings. Whenever possible, the same or like reference numbers and symbols are used throughout the drawings to refer to the same or like parts. The drawings are not necessarily to scale, and one skilled in the art will recognize where the drawings have been simplified to illustrate the key aspects of the disclosure.

The claims as set forth below are incorporated into and constitute part of this Detailed Description.

The entire disclosure of any publication or patent document mentioned herein is incorporated by reference, including U.S. patent application Ser. No. 13/463,322, entitled "Systems and methods for measuring the stress profile of ion-exchanged glass," and in U.S. Provisional Patent Application Ser. No. 61/706,891, entitled "Systems and methods for measuring birefringence in glass and glass-ceramics."

Figure 2A:
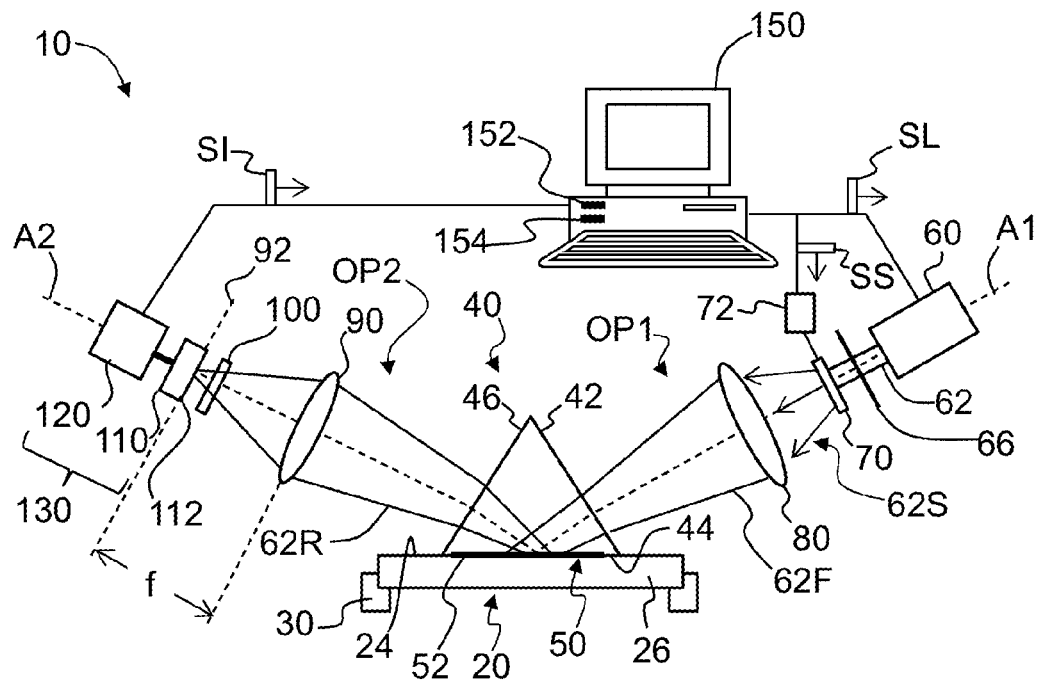
FIG. 2A is a schematic diagram of an example embodiment of a prism-coupling system that can be used to obtain improved contrast TM and TE mode spectra of a DIOX sample according to the methods disclosed herein.

FIG. 2A is a schematic diagram of an example prism-coupling system ("system") 10 suitable for carrying out the methods of measuring the TE and TM mode spectra of a DIOX sample 20 as disclosed herein. The sample 20 has a top surface 24 and a body or bulk portion 26 with a refractive index $n_s$. In one embodiment, system 10 includes a sample holder 30 configured to hold sample 20. In alternative embodiments, however, sample holder 30 is not required.

Figure 1A:
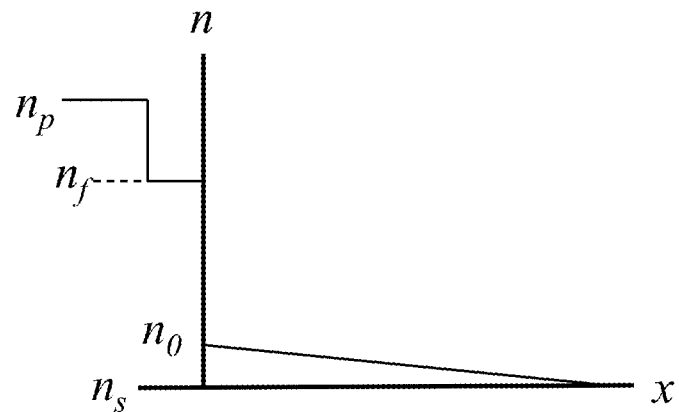
FIG. 1A is a plot of refractive index n vs. depth x into a glass sample, illustrating an example refractive index profile for a first ion-exchange process.
Figure 1B:
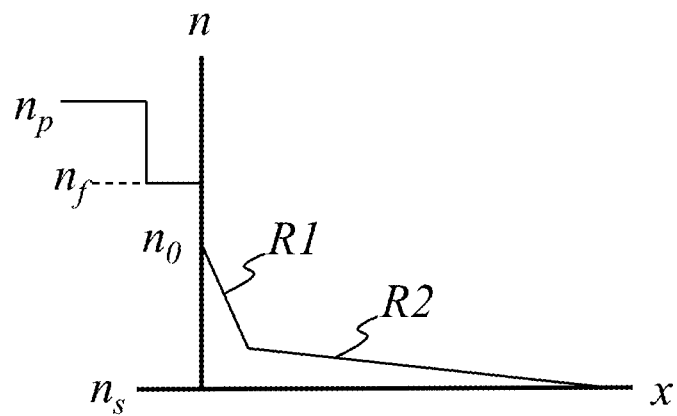
FIG. 1B is similar to the plot of FIG. 1A, but represents the refractive index profile after performing a second ion-exchange process, thereby creating a first steep and shallow profile region (R1) adjacent the sample surface followed by second profile region (R2) of less slope but greater depth into the sample than the first region.

In an example, sample 20 has undergone a DIOX process whereby two different types of ions have been exchanged through top surface 24, thereby changing the refractive index of the sample at (and near) the top surface to have a refractive index profile n(x) such as illustrated in FIG. 1B, wherein the profile has a steep region R1 closes to top surface with a maximum refractive index $n_0$ and a second less-steep region R2 that extends into the body down to the substrate index $n_s$. The refractive index profile n(x) may be different for s-polarized light (transverse electric, TE) than for p-polarized light (transverse magnetic, TM), which is polarized parallel to its plane of incidence. This process gives rise to birefringence at and near top surface 24 of sample 20. This birefringence is measured by system 10, and the resulting measurement can be used to calculate the stress (e.g., compressive stress CS) at (and near) top surface 24, and/or the stress profile S(x), using known techniques.

For example, one method of calculating the stress profile S(x) includes digitally capturing TM and TE guided mode spectra defined by the DIOX sample 20 using system 10. The method then includes determining positions of intensity extrema of the TM and TE guided mode spectra, and calculating respective TM and TE effective refractive indices from the positions. The method also includes calculating TM and TE refractive index profiles $n_{TM}(x)$ and $n_{TE}(x)$ from the effective refractive indices. This calculation can be performed using one of two approaches. The first approach includes performing an inverse WKB calculation based on TM and TE effective refractive indices, respectively. The second approach includes fitting calculated guided mode spectra to the TM and TE guided mode spectra using one or more assumed functions for $n_{TM}(x)$ and $n_{TE}(x)$. The method further includes calculating the stress profile $S(x)=[n_{TM}(x)-n_{TE}(x)]/$ SOC, where SOC is the stress-optic coefficient.

Measurements of stress and birefringence can be used for process and quality control in the manufacture of DIOX samples 20. Such samples can include chemically strengthened glass and glass-ceramics, similar to GORILLA® glass, made by Corning, Inc., of Corning, N.Y. Sample 20 may be in the form of a substrate, so that in the discussion below sample 20 is also referred to as substrate 20. In an example, substrate 20 is silica-based glass and contains at least one type of ion that can out-diffuse during an ion-exchange process.

The system 10 also includes a coupling prism 40 having an input surface 42, a coupling surface 44 and an output surface 46. The coupling prism 40 has a refractive index $n_p > n_s$. The coupling prism 40 is interfaced with sample 20 by bringing coupling-prism coupling surface 44 and sample top surface 24 into optical contact and thereby defining a sample—coupling prism interface ("interface") 50.

In an example embodiment, coupling prism 40 has a trapezoidal, curved or other cross-sectional shape instead of the triangular cross-sectional shape that is shown in FIG. 2A by way of illustration.

Figure 2B:
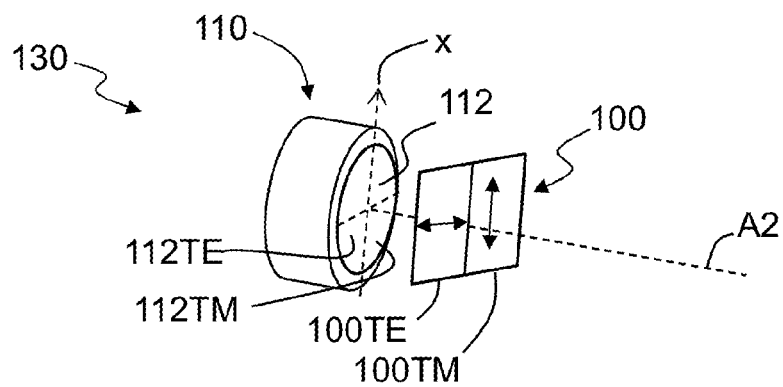
FIG. 2B is an elevated view of the example photodetector system of the surface-stress measurement system of FIG. 2A, showing an IR analog detector and a TE/TM polarizer.
Figure 2C:
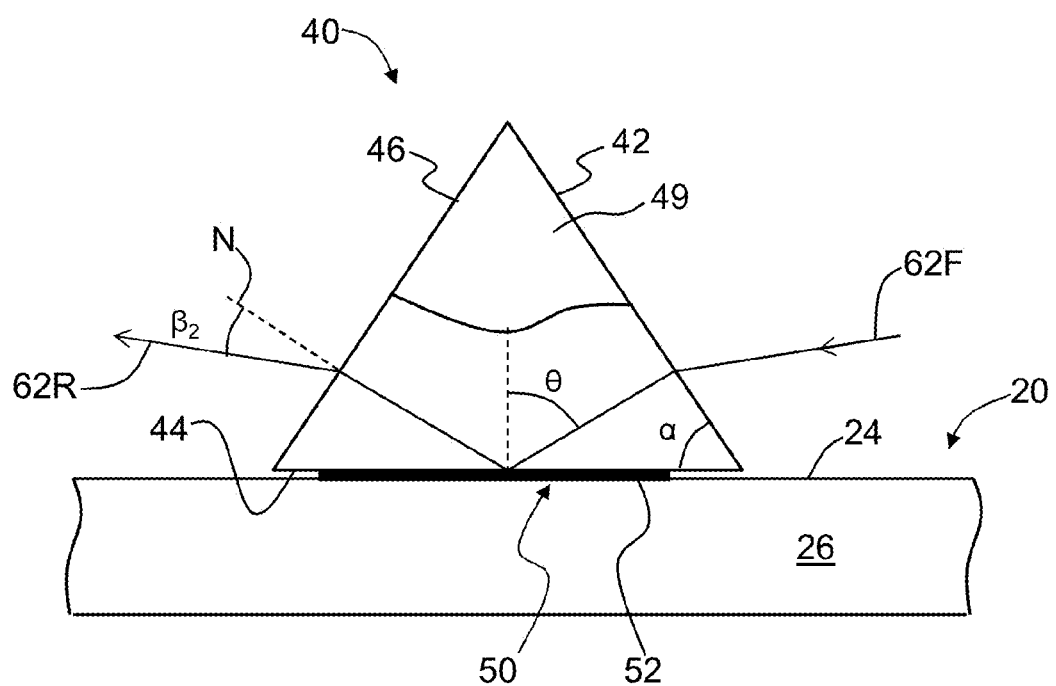
FIG. 2C is a close-up side view of the coupling prism and the DIOX sample of FIG. 2A, illustrating the key angles associated with the coupling prism and the focused and reflected light used in characterizing the surface stress profile.

FIG. 2C is a close-up view of coupling prism 40 and sample 20 that illustrates the key angles associated with the coupling prism and focused and reflected light 62F and 62R. In an example, coupling prism 40 is configured as an isosceles triangle in a cross-section. In an example, the isosceles triangle has a corner angle $\alpha=60°$. The focused light 62F incident upon a prism-sample interface 50 at an angle $\theta$ exits coupling prism output surface 46 at angle $\beta_2$ with respect to the surface normal N. These key angles can be used to calculate the effective indices and thus the refractive index profiles $n_{TM}(x)$ and $n_{TE}(x)$ discussed above in order to determine one or more stress characteristics of the DIOX sample 20.

A thin layer of interfacing fluid 52 is used to facilitate optical coupling between coupling prism 40 and sample 20 and is part of the prism-sample interface 50. Properties of and the select use of interfacing fluid 52 are discussed in greater detail below.

With continuing reference to FIG. 1, system 10 includes optical axes A1 and A2 that respectively pass through input and output surfaces 42 and 46 of coupling prism 40 to generally converge at prism-sample interface 50 after accounting for refraction at the prism/air interfaces. The system 10 includes, in order along axis A1, a light source 60 that emits measurement light 62 of wavelength λ, an optional optical filter 66 that may be alternatively included in the detector path on axis A2, an optional light-scattering element (i.e., diffuser) 70, and an optional focusing optical system 80 that forms focused (measurement) light 62F, as explained below. Thus, in an example of system 10, there are no optical elements between light source 60 and prism input surface 42. In an example, diffuser 72 operably connected to a driver 72 that moves (e.g., oscillates, vibrates, rotates, etc.) the diffuser in response to a control signal SS.

The system 10 also includes, in order along axis A2 from coupling prism 40, a collecting optical system 90 having a focal plane 92 and a focal length f and that receives reflected light 62R as explained below, a TM/TE polarizer 100, and a photodetector system 130. The axis A1 defines the center of an optical path OP1 between light source 60 and coupling-prism coupling surface 44. The axis A2 defines the center of an optical path OP2 between coupling surface 44 and photodetector system 130. Note that axes A1 and A2 may be bent at input and output surfaces 42 and 46, respectively, due to refraction.

In an example, photodetector system 130 includes an detector (camera) 110 and a frame grabber 120. In other embodiments discussed below, photodetector system 130 includes a CMOS or CCD camera. The photodetector system 130 includes a photosensitive surface 112. The photosensitive surface 112 resides in focal plane 92 of collecting optical system 90, with the photosensitive surface being generally perpendicular to axis A2. This serves to convert the angular distribution of light 62R exiting the coupling prism to a transverse spatial distribution of light at the sensor plane of camera 110.

Splitting photosensitive surface 112 into TE and TM sections 112TE and 112TM allows for the simultaneous recording of digital images of the angular reflection spectra (mode spectra) for the TE and TM polarizations of reflected light 62R. This simultaneous detection eliminates a source of measurement noise that could arise from making the TE and TM measurements at different times, given that system parameters can drift with time.

Example light sources 60 include lasers, light-emitting diodes, and broader-bandwidth sources such as hot-filament lamps and quartz lamps. Example operating wavelengths λ of light 62 generated by light source 60 can include visible and infrared wavelengths.

The system 10 includes controller 150, which is configured to control the operation of the system. The controller 150 is also configured to receive and process image signals SI from photodetector system 130 that are representative of captured TE and TM mode spectra images. The controller 150 includes a processor 152 and a memory unit ("memory") 154. The controller 150 may control the activation and operation of light source 60 via a light-source control signal SL, and receives and processes image signals SI from photodetector system 130 (e.g., from frame grabber 120, as shown).

In an example, controller 150 comprises a computer and includes a reading device, for example, a floppy disk drive, a CD-ROM drive, a DVD drive, a magnetic optical disk (MOD) device (not shown), or any other digital device including a network-connecting device, such as an Ethernet device (not shown), for reading instructions and/or data from a computer-readable medium, such as a floppy disk, a CD-ROM, a DVD, a MOD, a flash drive, or another digital source such as a network or the Internet. The controller 150 is configured to execute instructions stored in firmware and/or software (not shown), including signal-processing instructions for carrying out the surface birefringence/stress measurements disclosed herein. In examples, the terms "controller" and "computer" are interchangeable.

The controller 150 is programmable to perform the functions described herein, including the operation of system 10 and the aforementioned signal processing of image signals SI in order to arrive at a measurement of the stress characteristics of substrate 20, such as the stress profile S(x), birefringence, or compressive stress CS. As used herein, the term "computer" is not limited to just those integrated circuits referred to in the art as computers, but broadly refers to computers, processors, microcontrollers, microcomputers, programmable logic controllers, application-specific integrated circuits, and other programmable circuits, and these terms are used interchangeably herein.

Software may implement or aid in the performance of the operations of system 10 disclosed herein, including the aforementioned signal processing. The software may be operably installed in controller 150 and in particular in processor 152 and memory 154. Software functionalities may involve programming, including executable code, and such functionalities may be used to implement the methods disclosed herein. Such software code is executable by the general-purpose computer or by the processor unit described below.

In operation, the code and possibly the associated data records are stored within a general-purpose computer platform, within processor 152 and/or in memory 154. At other times, however, the software may be stored at other locations and/or transported for loading into the appropriate general-purpose computer systems. Hence, the embodiments discussed herein involve one or more software products in the form of one or more modules of code carried by at least one machine-readable medium. Execution of such code by processor 152 of computer system 150 or by the processor unit enables the platform to implement the catalog and/or software downloading functions in essentially the manner performed in the embodiments discussed and illustrated herein.

The computer 150 and/or processor 152 may each employ a computer-readable medium or machine-readable medium (e.g., memory 154), which refers to any medium that participates in providing instructions to the processor for execution, including, for example, determining an amount of surface birefringence/stress or the stress profile S(x) of sample 20. The memory 154 constitutes a computer-readable medium. Such a medium may take many forms, including but not limited to non-volatile media, volatile media and transmission media. Non-volatile media include, for example, optical or magnetic disks, such as any of the storage devices in any computer(s) operating as one of the server platforms discussed above. Volatile media include dynamic memory, such as the main memory of such a computer platform. Physical transmission media include coaxial cables, copper wire and fiber optics, including the wires that comprise a bus within a computer system.

Common forms of computer-readable media therefore include, for example, a floppy disk, a flexible disk, a hard disk, magnetic tape, flash drives and any other magnetic medium; a CD-ROM, a DVD and any other optical medium; less commonly used media such as punch cards, paper tape and any other physical medium with patterns of holes; a RAM, a PROM, an EPROM, a FLASH-EPROM and any other memory chip or cartridge; a carrier wave transporting data or instructions, cables or links transporting such a carrier wave, or any other medium from which a computer can read programming code and/or data. Many of these forms of computer-readable media may be involved in carrying one or more sequences of one or more instructions to processor 152 for execution.

System 10 may be a modified version of a commercial prism-coupling instrument, such as the FSM-6000 prism-coupling instrument made and sold by Orihara Industrial Co., Ltd., of Tokyo, Japan. The FSM-6000 instrument represents the state of the art in high-throughput non-destructive measurements of stress in flat ion exchanged glasses, and utilizes a prism 40 with a prism index $n_p$=1.72 at 589 nm. The FSM-600 uses an index-matching fluid having an index $n_f$=1.64. In the FSM-6000 instrument, the surface compressive stress (CS) is calculated from the effective indices of the first two transverse magnetic (TM) and the first two transverse electric (TE) modes, while the total number of observed modes is used along with the aforementioned effective indices of the first 2 modes for the depth of layer (DOL) calculation based on a linear refractive-index profile assumption.

Figure 3:
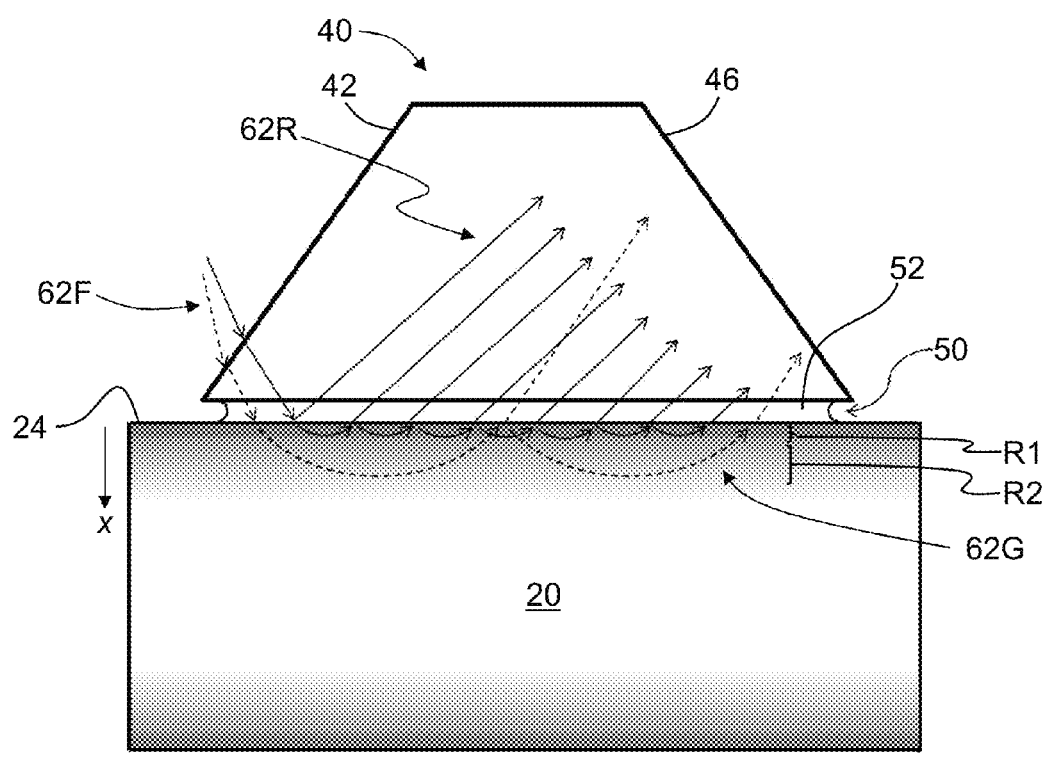
FIG. 3 is a cross-sectional view of the DIOX sample and the coupling prism of FIG. 2A and schematically illustrates the propagation of light within the two profile regions R1 and R2.

FIG. 3 is a cross-sectional view of an example DIOX substrate 20 and coupling prism 40 that schematically illustrates the propagation of guided light 62G within the two index profile regions R1 and R2 formed by the DIOX process. Interfacing fluid 52 can be applied to either the coupling surface of the coupling prism or the DIOX sample surface. When interfacing fluid 52 with an index higher $n_f > n_s$ is used to interface substrate 20 and the coupling prism 40 to form prism-sample interface 50 using conventional prism coupling, dark-line resonances corresponding to light propagation modes confined essentially within the shallow, steep region R1 of the index profile, are not observed or are difficult to observe because of their low contrast. Optical rays describing approximately coupling in, propagation in the steep region R1, and coupling out, are illustrated in FIG. 3 as solid-line arrows. The prism-coupling (mode) spectra of reflectivity of the prism-sample interface 50 as a function of incidence angle have high contrast only for those coupling resonances corresponding to modes spatially spread over the more extended, deeper index profile region R2, as illustrated by light rays described by the dashed-line arrows.

The reason for the substantial broadening (i.e., the decrease in contrast) of these coupling resonances (modes) is the excessive coupling between the modes and the prism, mediated by the interfacing fluid 52. In particular, the low-order modes confined close to the substrate surface 24 experience more bounces at the surface per unit propagation length. Consequently, these modes lose their energy much more quickly with propagation, experiencing substantial losses due to refraction of part of the light into the interfacing fluid 52 and coupling prism 40 (and out of the wave-guiding region R1) at every bounce.

This makes processing the TE and TM mode spectra for the DIOX substrate 20 problematic when trying to apply the prior art measurement methods such as those used by the FSM-6000 instrument. Also, the diminished mode-spectra contrast also renders problematic the use of methods for calculating the birefringence, including but not limited to the inverse Wentzell-Kramers-Brillouin (IWKB) method, and in fact produces incorrect results for the stress as well as the DOL.

Figure 4A:
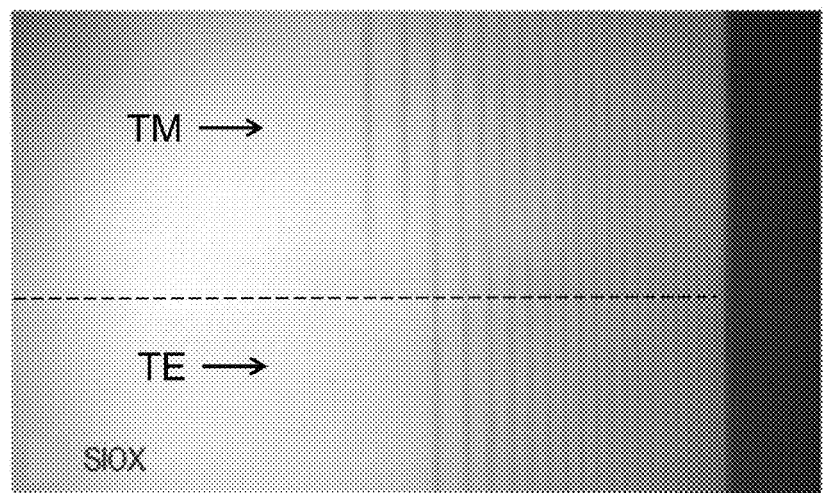
FIG. 4A is a captured image of TE and TM mode spectra obtained using a commercial version of the prism-coupling system of FIG. 2A for an example sample having undergone a single ion exchange (SIOX) using $K^+$ ions.
Figure 4B:
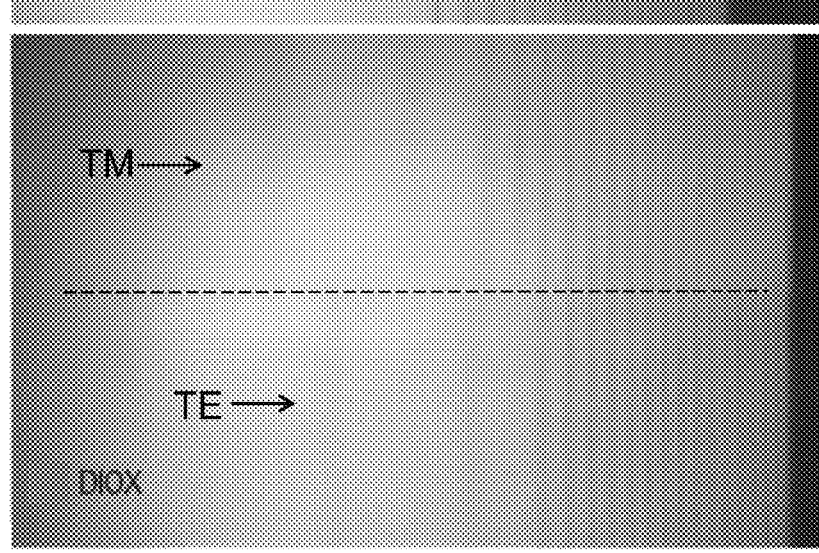
FIG. 4B is a captured image of TE and TM mode spectra obtained using a commercial version of the prism-coupling system of FIG. 2A for an example DIOX sample having undergone a $K^+$ ion exchange followed by a Ag+ ion exchange to create a refractive index profile similar to that of FIG. 1B.

FIG. 4A is a captured image of measured TE and TM mode spectra obtained using system 10 for an example sample 20 having undergone a single ion exchange (SIOX) process in a $KNO_3$ bath to add strengthening $K^+$ ions to the glass matrix. FIG. 4B is a captured image of measured TE and TM mode spectra obtained using system 10 for an example sample 20 having undergone a DIOX process, with a first, longer step (5 hours) in a $KNO_3$ bath and a second, shorter step (20 min) in $KNO_3$ bath to which as added 0.75 wt-% $AgNO_3$. The presence of the shallower Ag-enriched layer near the surface 24 that defines region R1 of the index profile is correlated with a significant reduction of the contrast of the dark spectral lines corresponding to the TE and TM modes in FIG. 4B, and in particular, the left-most two modes, for both the TM (top half of each spectrum) and TE (bottom half of each spectrum) polarization.

The methods disclosed herein seek to mitigate the problem of reduced contrast in the measured TM and TE mode spectra for DIOX sample 20. This is accomplished in part by using interfacing fluid 52 not so mainly as an index-matching or immersion medium between the sample and the coupling prism 40 as is done in the prior art, but instead as a substantially reflecting medium that provides for a stronger reflection at each bounce off of the sample-fluid interface, while not preventing coupling of light into the sample. In this manner, despite the large number of bounces per unit propagation length, the intensity of light coupled to the near-surface modes associated with region R1 will decay somewhat slower with propagation distance as compared to the prior-art case where a case where the oil index, while higher than the sample index, is not as high. This results in higher-contrast modes spectra, and hence narrower and deeper (e.g., sharper) coupling resonances than when interfacing fluid 52 is used to provide an oil with index-matching function.

Thus, instead of selecting the index $n_f$ of interfacing fluid 52 to be close to the mid-point between the prism index $n_p$ and the glass surface index $n_0$ (e.g. $n_p$=1.72, $n_0$=1.52, and $n_f$=1.64) as is conventionally done, in the present methods call for making the interfacing fluid index $n_f$ as high as possible to increase the reflection coefficient for each bounce (see FIG. 3).

Accordingly, an aspect of the disclosure is directed to a method of obtaining improved-contrast TM and TE mode spectra of a DIOX substrate 20 for at least the lowest-order modes (e.g., the first two modes), where the sample contains a region R1 of steep refractive index change near the sample surface 24, where the index predominantly decreases with increasing depth, and the index distribution n(x) in this near-surface region R1 is such that at the measurement wavelength λ, the following relationship for the normalized slope $$\frac{\lambda}{n}\frac{dn}{dx}$$

holds:

$$\left|\frac{\lambda}{n}\frac{dn}{dx}\right| \geq 0.0004,$$

and in particular, $$\left|\frac{\lambda}{n}\frac{dn}{dx}\right| \geq 0.0005.$$

Further in the method, coupling prism 40 with refractive index $n_2$>1.780 is used to couple light 62F to the confined optical modes of substrate 20, and interface fluid 52 having a high refractive index $n_f$≤1.72 is used to interface the coupling prism and the sample to enable optical coupling therebetween. In an example embodiment, the refractive index $n_f$ of the interfacing fluid 52 is greater than the surface index $n_0$ of the sample 20 by at least 0.15, and in particular, by at least 0.17.

In a more specific embodiment, $n_f$ differs from $n_p$ by no more than 0.03, and $n_p$>1.7.

In another preferred embodiment, $n_f$ differs from $n_p$ by no more than 0.01.

According to an example method, interface fluid 52, when used with coupling prism 40 having a prism index of $n_p$=1.72, has a refractive index $n_f$ in the range from 1.69≤$n_f$≤1.8 to obtain measurements of DOIX sample 20 that have acceptable standard deviation for the CS (in an example, <10 MPa). Such measurements can be performed about as fast as measurements of for SIOX samples, including regular chemically strengthened glass that is not anti-microbial. In this range, the breadth and maximum coupling efficiency for the coupling resonances associated with optical modes of propagation confined inside the steep near-surface region of substrate 20 have improved contrast, which allows for the stress in the DIOX sample 20 to be characterized to within acceptable limits of error and time.

In experiments conducted using system 10 to measure a DIOX sample and using index-matching oil with index $n_f$=1.64, optical modes were confined near the surface in region R1. However, the corresponding mode spectra had dark lines (fringes) that were too broad and shallow to allow an accurate manual or automated measurement of the compressive stress. Experiments were then conducting using an interfacing fluid 52 in the form of an oil with $n_f$=$n_p$=1.72 and the mode spectra had improved contrast associated with narrower and deeper coupling resonances. The result was improved precision of the stress measurement.

The improvement was found particularly helpful when the slope of the index profile satisfied the approximate inequality:

$$\left|\frac{\lambda}{n}\frac{dn}{dx}\right| \leq 0.0013 \qquad (1)$$

The absolute value is used in Eq. 1 because the slope is actually negative (index n decreases with increasing depth x). For higher slopes, the improvement was even more significant, but the coupling spectra with standard oil of n=1.64 were of such poor quality that even the substantially improved spectra with the higher-index-oil (n=1.72) were difficult to process automatically, and exhibited substantial standard deviations (>30 MPa) for the stress measurements. In the described examples, the refractive index of the glass substrate is about 1.5, and the glass surface index was typically about 1.53.

In cases where $$\left|\frac{\lambda}{n}\frac{dn}{dx}\right| \leq 0.0004,$$

and in particular $$\left|\frac{\lambda}{n}\frac{dn}{dx}\right| \leq 0.0003,$$

use of the standard oil with $n_f$=1.64 usually produces measurement results of adequate precision, since the resonances are observed with adequately narrow dark lines.

Note that stress-measurement equipment based on prism coupling, such as FSM-6000, does not show improved precision of measurements for normal SIOX chemically strengthened glass if the oil index is increased above the typical $n_f$=1.64, to values such as 1.72, or even 1.78, as described in the invention and illustrated at the top portion of FIG. 7. Hence, it was not obvious from the state of the art that the use of higher oil index would help substantially improve the measurement precision when measuring anti-microbial chemically strengthened samples. Indeed, as mentioned earlier, for very high normalized slopes such as for $$\left|\frac{\lambda}{n}\frac{dn}{dx}\right| \geq 0.0013,$$

the increase in contrast that was observed was not adequate for practical measurements. The present inventors have discovered a relatively narrow region of index profiles having the above specified range of normalized absolute slopes between about 0.0004 and 0.0013, for which the invention is readily applicable for practical use.

Figure 5A:
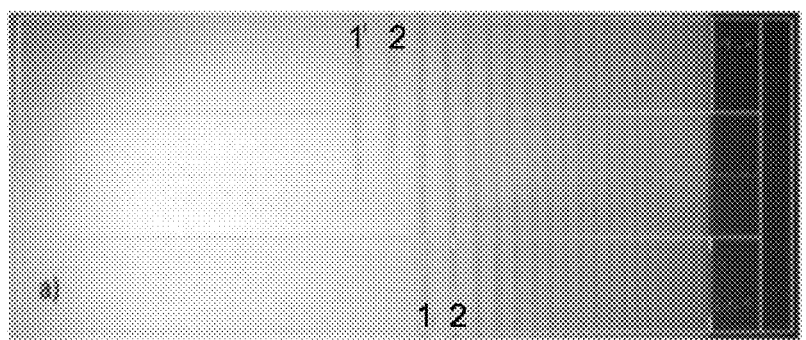
FIG. 5A is a captured mode spectrum image that shows the automatic detection of the relevant lowest-order modes and position of the critical angle $\theta_C$ on the above-described SIOX sample using a commercial version of the prism-coupling system of FIG. 2A, showing the correct identification of the modes.
Figure 5B:
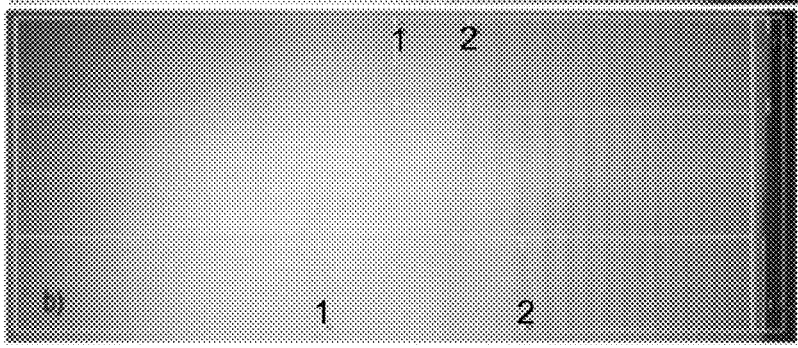
FIG. 5B is a captured mode spectrum image that shows the automatic detection for the above-described DIOX sample using a commercial version of the prism-coupling system of FIG. 2A, wherein the decreased contrast of the coupling spectra has led to erroneous identification of the first and second TM mode, and of the second TE mode.

FIG. 5A is a captured mode spectrum image that shows the automatic detection of the relevant lowest-order modes and the position of critical angle $\theta_C$ on the above-described SIOX sample. FIG. 5B is also a captured mode spectrum image that shows the automatic detection for the above-described DIOX sample with $Ag^+$, using interfacing fluid 52 in the form of an oil with $n_f=1.64$. The decreased contrast between the spectra of FIG. 5A versus FIG. 5B has led to the erroneous identification of the first and second TM mode, and of the second TE mode, which subsequently resulted in an incorrect calculation of the CS and DOL.

Figure 5C:
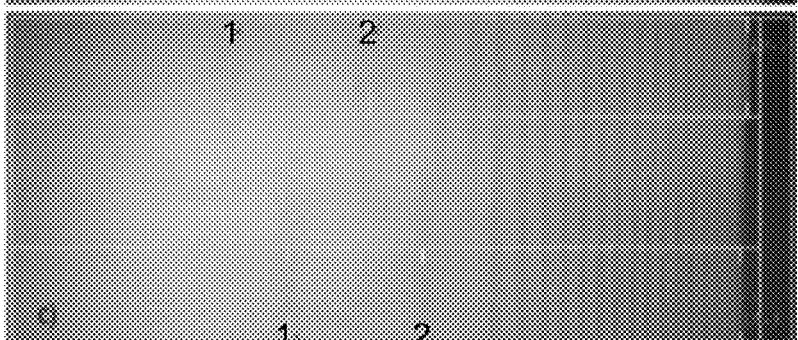
FIG. 5C is a captured mode spectrum image that shows the automatic detection for the DIOX sample using a commercial version of the prism-coupling system of FIG. 2A but with an interfacing fluid in the form of an oil having $n_f=1.775$, resulting in mode spectra with improved contrast, which enables the correct automatic identification of the modes.

FIG. 5C is a captured mode spectrum image that shows the automatic detection for the above-described DIOX sample 20. The mode spectrum was captured using an interfacing fluid 52 in the form of an oil with $n_f=1.775$, resulting in TM and TE mode spectra with improved contrast. The improved contrast in turn enabled the correct automatic identification of the modes and subsequently a suitably accurate determination of the stress profile. The pure-substrate index was about $n_s=1.50$, while the surface refractive index after SIOX is about $n_0=1.515$, and after DIOX it is about $n_0=1.53$.

FIG. 5C shows how one of the aspects of the present invention helps mitigate the line-broadening problem to a level where automated measurements can be obtained correctly much more often for samples of current interest as anti-microbial chemically strengthened glass. The same DIOX sample, measured using index of 1.775, produces a coupling spectrum of somewhat better contrast, and proper mode identification by the software results in correctly calculated CS and DOL.

To enable capturing the entire mode spectrum in a single image frame, the focal length of system 10 can be reduced, e.g., from the standard 200 mm to 100 mm, approximately doubling the angular breadth associated with the captured image. This results in approximately doubling the effective index range measured in a single frame, to about 0.03 RIU (refractive-index units), and was used to capture the spectra of FIGS. 4, 5, and 6.

In an example, the slope of the steep portion of the profile (region R1) of DIOX sample 20 satisfies $$0.0005 \leq \left|\frac{\lambda}{n}\frac{dn}{dx}\right| \leq 0.0009,$$

where $\lambda$ is the measurement wavelength and n is the approximate refractive index of the measured glass.

FIGS. 6A through 6D are captured images of TE and TM mode spectra of the above-described DIOX sample as obtained using a commercial version of the prism-coupling system of FIG. 2A, using interfacing fluid 52 in the form of different oils having refractive indices $n_f$ of 1.64, 1.72, 1.775 and 1.8, respectively. The angular coupling (dark-line) mode spectra were obtained using system 10 when measuring a DIOX substrate 20 that was first ion-exchanged in a $KNO_3$ bath, and then ion exchanged in a $KNO_3$ bath containing 0.75 wt-% $AgNO_3$, such that the Ag+ ions penetrate several times shallower than the K+ ions (e.g., K+ penetrating to a depth of about 35 microns and Ag+ penetrating to a depth of between 8 and 10 microns). The resulting DIOX sample 20 was thus anti-microbial. The prism index was np=1.72, and $n_f$ was sequentially increased from 1.64, 1.72, 1.775, and 1.8. The measurement wavelength was 595 nm.

While the entire mode spectrum is observed (TM modes on top half of each spectrum, and TE on bottom half), a slight narrowing of the spectral lines can be observed with increasing index $n_f$, particularly for the left-most TM and TE lines. The software of the FSM-6000 commercial instrument was able to properly identify the low-order modes in less than about 5% of replicate measurements of the same sample when using $n_f=1.64$, but identified them in more than about 20% of replicate measurements when using $n_f=1.72$ and higher.

Figure 7A:
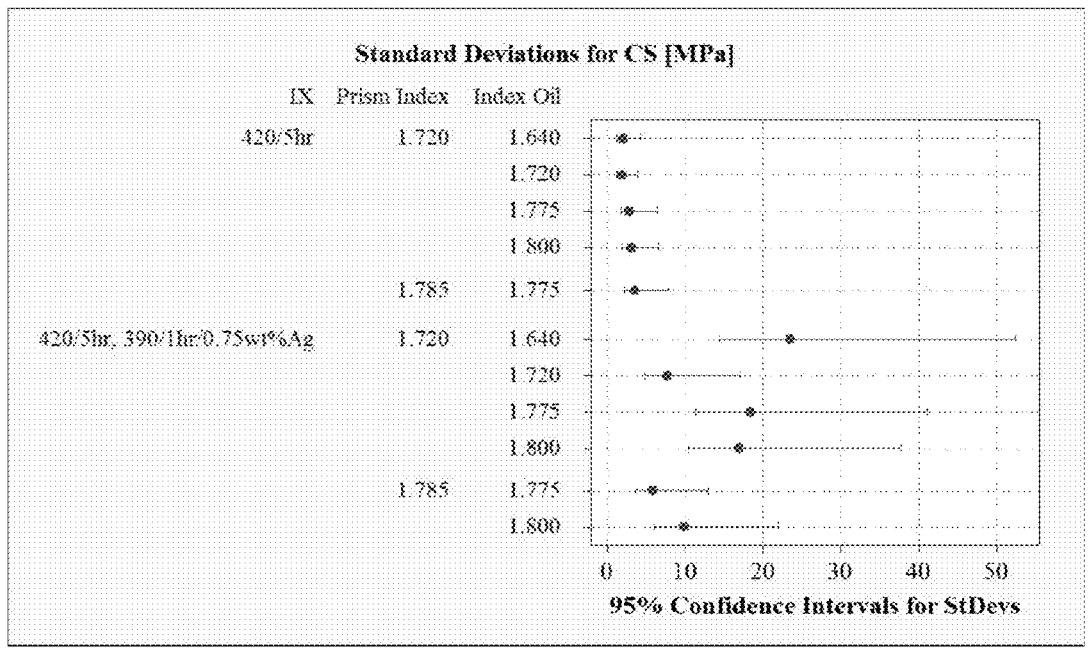
FIG. 7A is a plot of the standard deviations obtained from measuring the compressive stress CS for SIOX and DIOX samples.

FIG. 7A is a plot of the standard deviations obtained from measuring the above-described SIOX and DIOX samples. The deviations were obtained from 12 measurements per measurement condition, excluding measurements for which the instrument improperly identified any of the lowest-order modes. While using higher-index oil does not reduce the standard deviations for the regular 1-step SIOX sample, it does reduce the standard deviation of measurements for the two-step sample with Ag. In particular, the oils with index higher than 1.64 have lower standard deviations.

In addition, the standard deviations are smaller when the oil index is closer to the prism index. The higher-index prism with $n_p=1.785$ is non-standard. It was mounted using a makeshift mount, which is likely to have increased the standard deviations for that prism compared to what they could have been if it had the same dimensions and were mounted in the way the equipment is supposed to operate. Nevertheless, the measurements of the DIOX sample 20 with high-index coupling prism 40 and high-index oil 52 show reduced standard deviation for the measurement of CS as compared to the measurement taken with the coupling prism of $n_p=1.72$ combined with the standard index-matching oil having $n_f=1.64$.

In addition to the significant difficulty for automated processing of the mode spectra obtained using $n_f=1.64$, the standard deviation of the compressive stress CS was undesirably high at about 25 MPa. On the other hand, the CS standard deviation decreased significantly when using interfacing fluid 52 with $n_f=1.72$ and higher (FIG. 7A, bottom half of data). It is also observed in FIG. 7A that when $n_f$ is substantially different from the prism index $n_p$ (e.g., by 0.08 or 0.055), the standard deviation is higher than when it is closer to the prism index, even when the $n_f > n_p$. In the case when $n_f > n_p$, an increase in standard deviation may be due to a possible weak resonances between reflections from the two interfaces on either side of the interfacing fluid. Such resonances will cause a small variation in intensity across the image, which will depend on the thickness of the interfacing fluid, and may affect slightly the positions of the coupling resonances as measured by the software, even when the modes are properly identified.

Figure 7B:
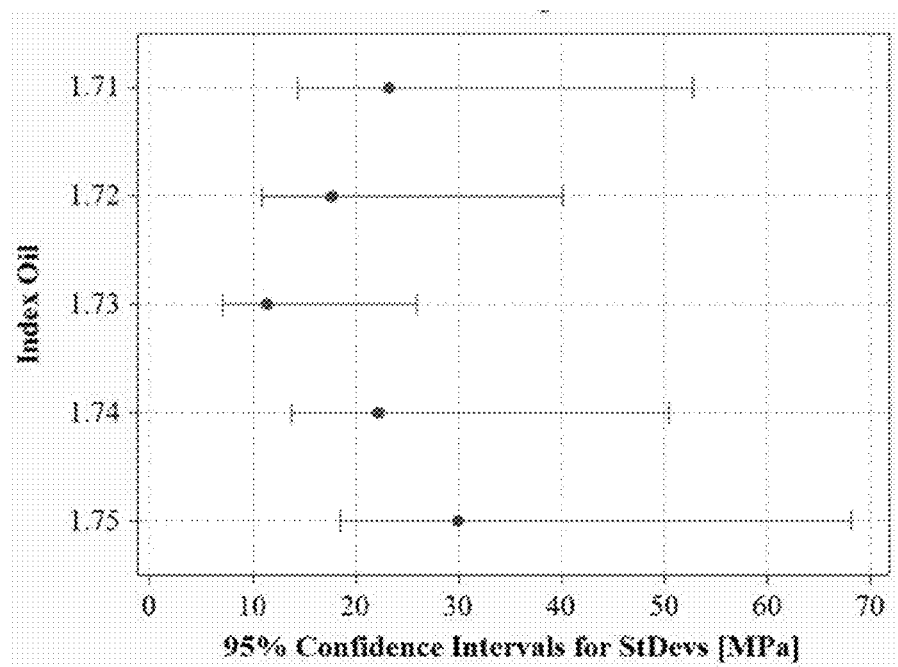
FIG. 7B is a plot similar to FIG. 7A for the same DIOX sample but using a finer series of interfacing fluids wherein the fluid index $o_f$ was varied from 1.71 to 1.75 for a prism index $n_p$ of 1.72.

FIG. 7B is a plot similar to FIG. 7A for the same DIOX sample but using a finer series of interfacing fluids wherein the fluid index $n_f$ was varied from 1.71 to 1.75 for a prism index $n_p$ of 1.72. The data of FIG. 7B show that the standard deviation is minimized for a fluid index $n_f$ that is slightly higher (by 0.01) than the prism index $n_p$.

In the case when $n_f < n_p$, in addition to the such weak interference effects, the stronger broadening of the coupling resonances due to the index-matching effect of interfacing fluid 52 may be leading to the even higher standard deviations, in addition to the increased difficulty in automatic processing.

Numerical simulations were performed that showed that further increases in $n_f$ up to 2.1 would allow for moderate improvement of the contrast of low-order-mode coupling resonances.

Figure 8:
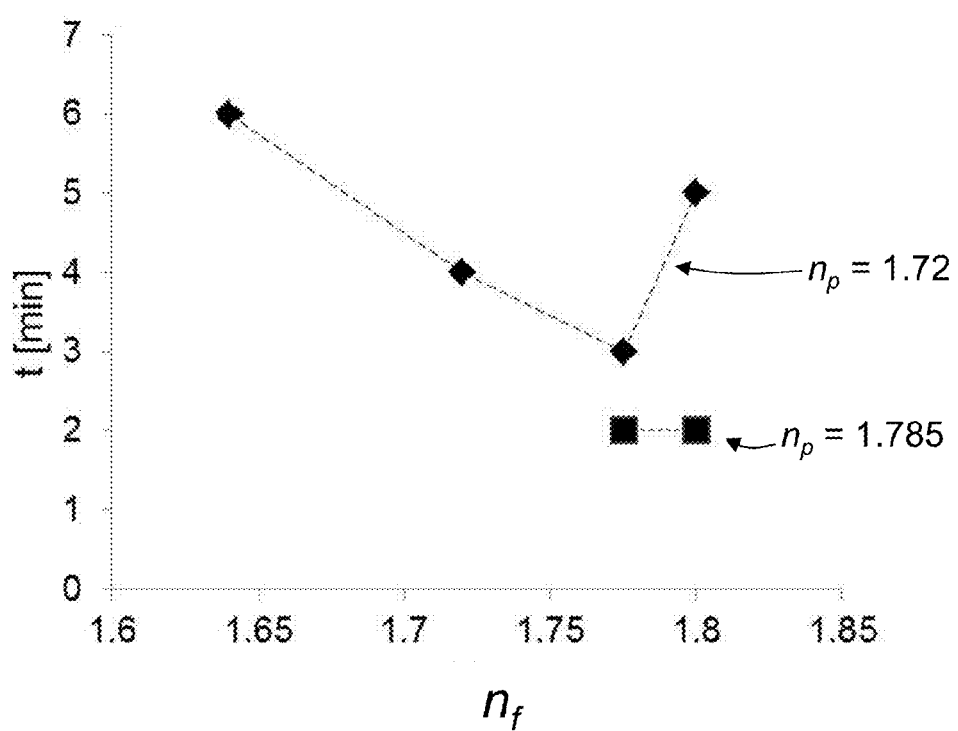
FIG. 8 is a plot of the time (minutes) vs. oil refractive index $n_f$ showing the amount of time for making measurements for SIOX and DIOX samples.

FIG. 8 is a plot of the time (minutes) vs. refractive index $n_f$ and shows the amount of time it takes to make twelve successful measurements for the aforementioned DIOX sample with automatic mode identification, for two different prism indices $n_p = 1.72$ and 1.785. The amount of time included sample re-load as performed by an experienced operator. These measurement times were obtained using the $Ag^+$ and $K^+$ DIOX substrate discussed above. A successful measurement was one where the image-processing software in controller 150 correctly identified the first and second mode, and the transition for critical angle $\theta_C$, for each of the TE and TM spectra, and calculated correct CS and DOL values.

Incorrect automatic identifications of the modes were rejected, as well as cases where the software produced an error message indicating inadequate contrast or improper distribution of fringe spacing. Adjustment of illumination by light source 60 was used to find a condition where the software successfully processed the captured the mode-spectra image. The relatively minor change in contrast observed visually when $n_f$ is increased actually leads to significant decrease of the average measurement time. In addition, using a higher-index coupling prism 40 (e.g., $n_p = 1.785$) with similarly higher-index interfacing fluid 52, further reduces the average measurement time.

FIGS. 7A and 7B also show that increasing the refractive index $n_f$ of the interfacing fluid to be closer to the coupling prism refractive index $n_p$ when measuring a SIOX sample 20 provides no benefit, and in fact increases the standard deviation of the CS measurement. Thus, it is non-intuitive that doing the same thing when measuring a DIOX sample 20 would improve the accuracy of the measurement. Yet, the data of FIGS. 7A and 7B indicate that the CS measurement has a decreased standard deviation when $n_f$ approaches or equals $n_p$.

Thus, in an example embodiment, $0.075 \leq n_f - n_p \leq 0.0125$, and more particularly, $n_f - n_p \approx 0.01$, and even more particularly $n_f - n_p = 0.01$. In another example embodiment, $-0.01 < n_f - n_p < 0.02$.

Non-uniform illumination of prism-sample interface 50, and in particular a significant angular non-uniformity of the illumination, may contribute to an increased standard deviation when calculating the compressive stress CS in cases where measurements of sample 20 show broadened lines of the mode spectra. An example of such a case is when sample 20 has refractive index profile n(x) with a relatively steep near-surface region, such as described above in connection with performing a DIOX process. The increase in standard deviation may be substantial when the non-uniform illumination is adjusted between measurements to help achieve adequate contrast of the measured mode spectra for enabling automated mode detection and processing by controller 150 of system 10.

With reference again to FIG. 2, in an example embodiment, a diffuser 48 is optionally used in system 10 to reduce the standard deviation for the compressive stress CS. The diffuser 48 is disposed along axis A1 between light source 60 and input surface 42 of coupling prism 40. In an example, diffuser 48 resides at an axial distance d48 from input surface 42, wherein $d48 \leq 4$ cm.

An exemplary diffuser 48 comprises or consists of a glass plate with one or two matte surfaces. In an example, the one or two matte surfaces may be obtained by grinding the plate with sand paper or a grinding tool, or using sand blasting. In an example, aforementioned sand paper may have grit size 125 or 220 for optimum performance.

In an embodiment, a portion diffuser 48 may be opaque to help increase the contrast for some of the coupling resonances. In particular, a portion of the side of diffuser 48 closest to coupling prism 40 may be blocked or blackened. This embodiment for diffuser 48 may be preferred in some cases where non-uniformity of measurement light 62F may be problematic, but even more problematic may be the low fringe contrast, particularly for the lowest-order modes. The standard deviation of the measurement is affected by both.

Passing focused beam 62F through diffuser 48 prior to the focused beam entering coupling prism 40 improves the angular uniformity of the beam. This in turn helps reduce variations of the location of the intensity extrema (minima or maxima) associated with resonances corresponding to discrete propagation modes of light 62 in the region R1 of increased refractive index of sample 20 (see FIG. 3). Such variation may be caused by changing the illumination to optimize the contrast for automated mode detection and processing by software in controller 150.

In an example, more than one diffuser 48 may be employed, wherein one of the diffusers is diffuser 48 that resides at distance d48 as defined above, while the other diffuser resides outside of this distance, i.e., greater than 4 cm from input surface 42 and thus closer to light source 60 and thus upstream of diffuser 48. In an example, the second diffuser is the aforementioned diffuser 70. Diffuser 70 is often used in prior art prism-coupling systems and is arranged close to light source 60.

Measurements taken on samples 20 using system 10 with two diffusers 48 and 70 showed a decrease of more than 20% of the CS standard deviation where the surface index $n_0$ increase was greater than about 0.02. The CS standard deviation decrease is compared to measurements performed on system 10 that only included the single diffuser 70. When making the above-described measurements, system 10 was configured such that distance d48=2 cm.

In an example embodiment, diffuser 48 may be attached to or otherwise placed in contact with input surface 42 of coupling prism 40. In another embodiment, diffuser 48 can be formed integrally on or with input surface 42, e.g., by roughening the input surface or otherwise turning a smooth input surface into a diffusing surface. In an example, diffuser 48 may be a scattering film place in intimate contact with input surface 42.

Controlled Illumination of the Prism-Sample Interface

The TM and TE mode spectra can have poor contrast when the mode coupling is strong. The poor contrast for the low-order, strongly-coupled modes can lead to a large standard deviation when measuring stress in the presence of noise. This is particularly true for DIOX samples, where chemical strengthening is first obtained through K for Na ion exchanged, and anti-microbial efficacy is enabled through a second ion exchange that introduces in a near-surface region of the glass.

Without being limited by theory, it is believed that the poor contrast for the low-order modes is due to two main mechanisms. The first relates to the broadening of the coupling resonances through a relationship between coupling strength and resonance width that is equivalent to the Kramers-Kronig relations. The second mechanism relates to the balance between light coupling into the guided modes of the ion-exchanged region, and light coupling from these guided modes back to the prism. In particular, when dark-line measurements are performed in the angular spectrum of reflection from the prism-sample interface, the measurement relies on light coupling into the guided modes to be absent in the reflection spectrum, thus resulting in a dark line at the corresponding angle. If light couples back from a particular guided mode to the prism, then it ends up increasing intensity at the location of the dark line on the detector that corresponds to the angle of coupling of that mode, resulting in reduced contrast for the resonance of that mode.

Figure 9:
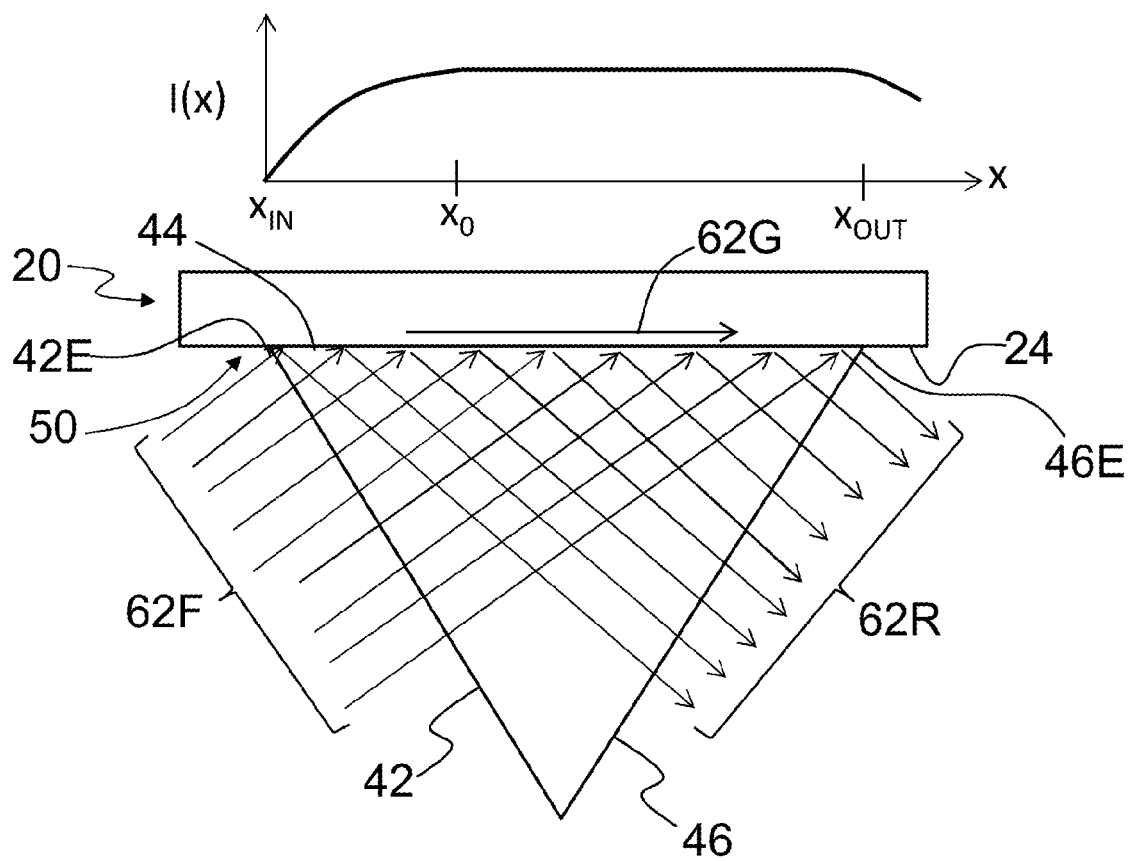
FIG. 9 is a schematic diagram of coupling prism interfaced with a sample and including a plot of the intensity I(x) of the light coupled into the waveguide region of the sample.

FIG. 9 is a schematic diagram of coupling prism 40 interfaced with sample 20 and showing the incident light 62F and reflected light 62R reflecting from prism-sample interface 50 in a prior art configuration. FIG. 9 includes a plot of the intensity I(x) of the light 62F coupled into regions R1 and R2 (see FIG. 3) that define an optical waveguide in sample 20 (see also FIG. 3). The direction along the prism-sample interface 50 is the X-direction, with the +X direction being the general direction of light travel. The light traveling in sample 20 as a guide wave is the aforementioned guided light 62G. The plot of intensity I(x) includes a location $x_{IN}$ associated with an input edge 42E of coupling surface 44 defined by input surface 42 and a location $x_{OUT}$ associated with an output edge 46E of coupling surface defined by output surface 46. For the purpose of the present discussion, edges 42E and 46E represent input and output ends of prism-sample interface 50.

Consider by way of example that the amplitude of the electric field of light 62F at the prism-sample interface 50 contributed by the illuminating wave at a given illumination angle is uniform along the prism-substrate interface. In this case, the intensity I(x) of light 62F coupled into sample 20 increases in the +X direction as more light couples into the sample. As the amount of guided light 62G traveling in sample 20 increases distance in the +X direction, light starts coupling back out of the prism as reflected light 62R, and the rate of increase of the intensity I(x) of guided light 62F decreases. If the coupling is strong, a condition can occur where a saturation of the intensity I(x) of guided light 62G is obtained at a location $x_0$ somewhere between the input and output edges 42E and 46E of the prism-sample interface 50. For positions $x > x_0$ the intensity I(x) is substantially constant because the amount of light 62F coupling into sample 20 is about the same as the amount of reflected light 62R that couples out of the sample. Reflected 62R from locations with $x > x_0$ does not contribute a useful mode spectra signal, but it does increase the illumination background, which leads to a decrease in contrast of the TM and TE mode spectra.

Figure 10:
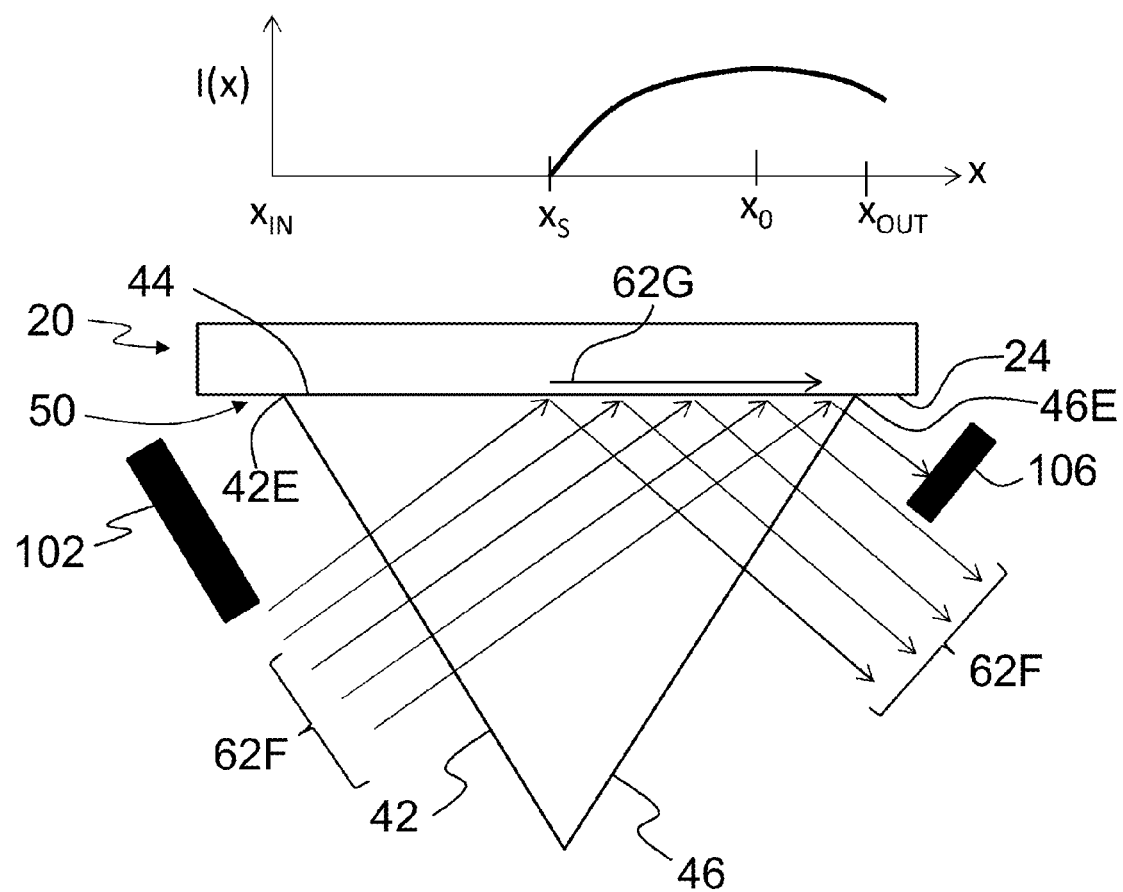
FIG. 10 is similar to FIG. 9 and shows an example embodiment that includes light-blocking members that reduce the amount of reflected background light from the prism-sample interface that reduces the contrast of the measured TM and TE mode spectra.

FIG. 10 is similar to FIG. 9 and shows a first light-blocking member 102 arranged adjacent input surface 42 of coupling prism 40 and a second light-blocking member 106 arranged adjacent the output surface 46 of the coupling prism. Light-blocking member 102 is arranged so that it blocks the portion of input light 62F that would be incident upon the prism-sample interface 50 closet to input edge 42E. In the plot of I(x) in FIG. 10, the blocked portion of prism-sample interface as defined by light-blocking member 102 is the region $x_{IN} \leq x < x_s$, where $x_S$ represents the starting location where input light 62F is incident upon the prism-sample interface.

The resulting intensity profile I(x) has a reduced constant-intensity region for $x > x_0$, which reduces the amount of background reflected light 62R reaching photodetector system 130. The reduction in background reflected light 62R results in an increased contrast for the TM and TE mode spectra. Light-blocking member 104 is optional and further serves to reduce the amount of unwanted reflected light 62R from reaching photodetector system 130.

The use of light-blocking member 102 may result in the broadening of some of the spectral lines of the TM and TE mode spectra due to the decrease in the effective beam size relative to the total size of the prism-sample interface 50. Also, part of the angular spectrum associated with the low-order TM and TE modes may experiences a decrease in intensity as compared to the high-order modes. This can lead to a substantial and varying slope of the intensity background as a function of angle, against which the dark spectral lines corresponding to the guided modes are detected. In turn, it may introduce some error in the measurements due to slight shifting of the positions of the intensity minima corresponding to the modes. Nevertheless, the overall benefit of obtaining increased TM and TE mode contrast generally outweighs the above-mentioned side-effects.

Figure 11A:
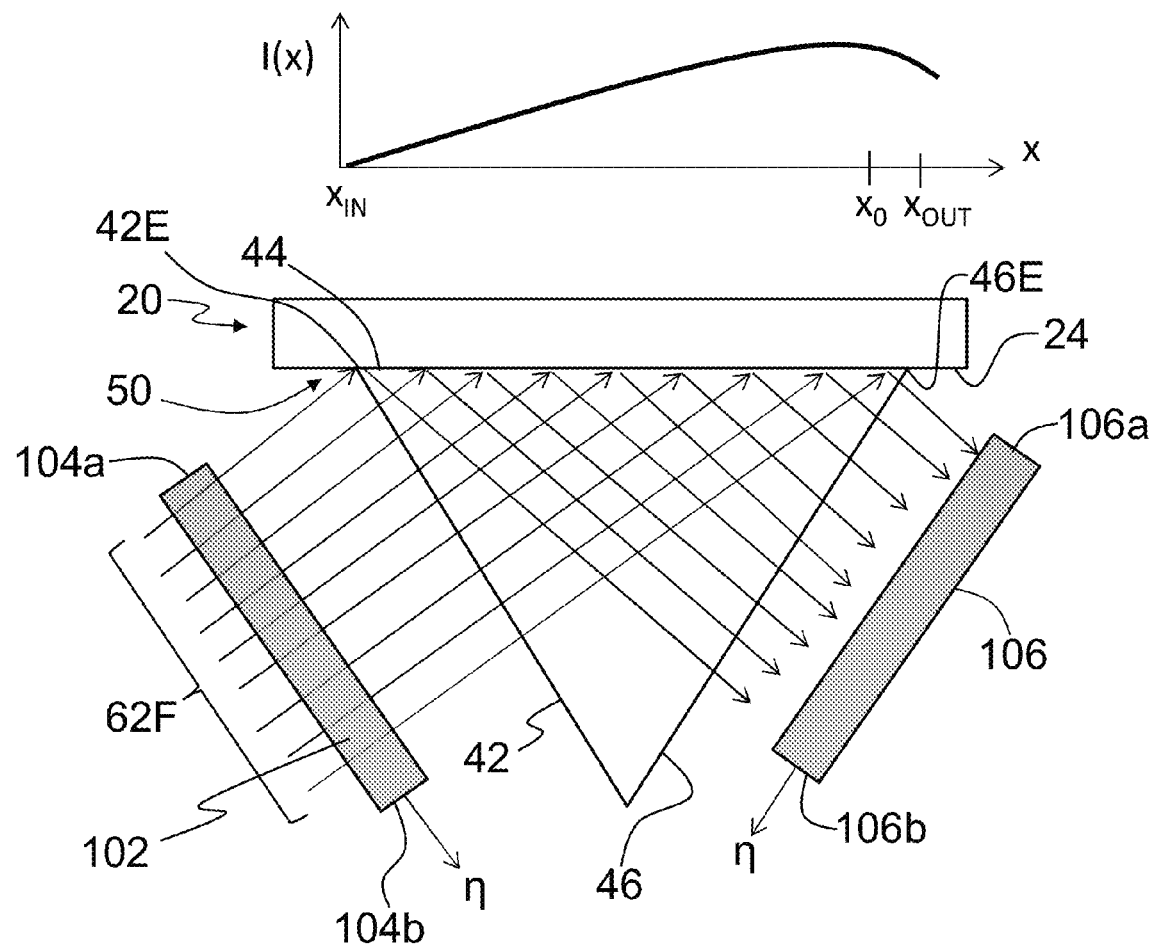
FIG. 11A is similar to FIG. 10, but wherein the light-blocking members have a graded transmittance.
Figure 11B:
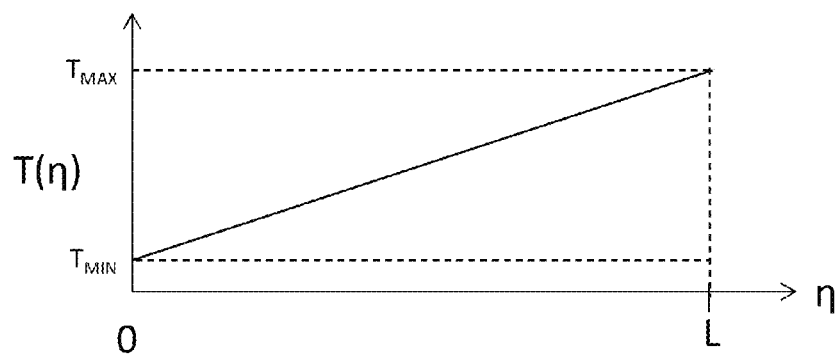
FIG. 11B is a plot of $T(\eta)$ vs. $\eta$, showing the graded transmittance of FIG. 11A.

FIG. 11A is similar to FIG. 10 and illustrates an example embodiment wherein light-blocking member 102 is shown oriented along a direction η and only blocks a portion of input light 62F. In an example, light-blocking member 102 has graded transmittance T(η) that increases with increasing η, as illustrated in the plot of T(η) vs. η of FIG. 11B, wherein L is the length of the light-blocking member as measured from a first end 104a at η=0 to a second end 104b at η=L. In an example embodiment, the transmittance T(η) ranges from a minimum value $T_{MIN}$ at η=0 (first end 104a) to a maximum value $T_{MAX}$ at η=L (second end 104b). In an example, the transmittance T(η) varies linearly between $T_{MIN}$ and $T_{MAX}$. In other examples, transmittance T(η) varies monotonically from $T_{MIN}$ to $T_{MAX}$. In an example, $T_{MIN}=0$ and $T_{MIN}=1$ (i.e., 100% transmittance). In an example, the transmittance T(η) can have a flat region of uniform transmittance, e.g., a region where TMIN is constant from say η=0 to η=L/5.

Sending input light 62F through light-blocking member 102 of FIG. 11A serves to provide gradient illumination of prism-sample interface 50. For improved detection of dark spectral lines, a positive gradient for input illumination 62F is employed, where intensity increases in the X-direction. In this case, the region of increasing amplitude of the electric field inside the waveguide of sample 20 is stretched in the X-direction toward edge 46E. The continuously increasing illumination intensity I(x) helps reduce or eliminate the adverse effects on the contrast of the TM and TE spectra due to background reflected light 62R associated with the aforementioned constant-intensity illumination.

In an example, light-blocking member 106 with edges 106a and 106b and having a gradient light transmittance is employed, i.e., the light blocking occurs adjacent the output surface 46 of coupling prism 40 rather than adjacent the input surface 42. The intensity I(x) in the waveguide of sample 20 will be similar to that of FIG. 9 in that it will have an extended region of near-constant intensity. However, the gradient-transmittance light-blocking member 106 will have low-transmittance on the side 106a that is closest to prism-sample interface 50. This arrangement provides strong attenuation of the constant-intensity reflected light 62R. At the same time, the higher-transmittance end of light-blocking member 106 allows for substantial transmission of reflected light 62R coming from the high-contrast region $x < x_0$.

Figure 12A:
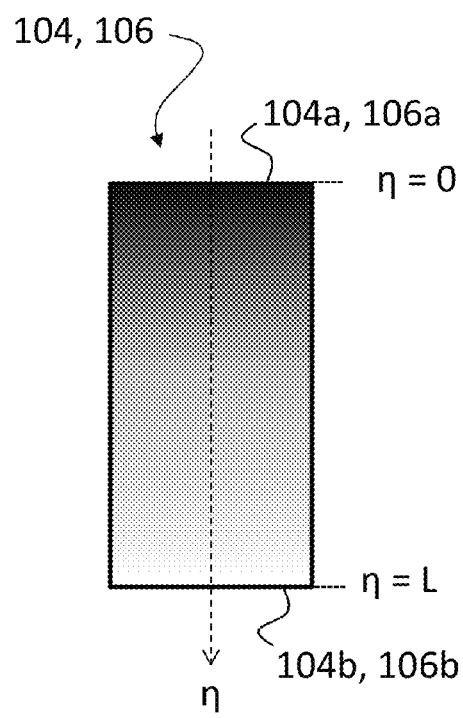
FIGS. 12A and 12B are front-on views of example light-blocking members that have a graded transmittance.
Figure 12B:
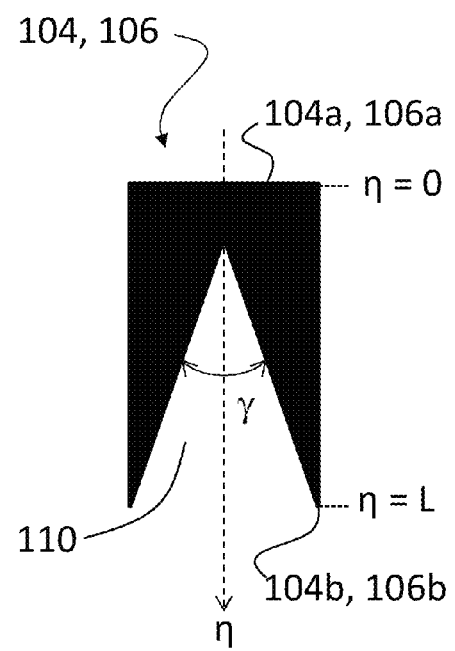

FIGS. 12A and 12B are front-on views of example light-blocking members 104 or 106. The light-blocking member 104 or 106 of FIG. 12A as a gradient transmittance T(η) defined by a gradient absorption profile. Such a light-blocking member 104 or 106 may be formed from glass that either a graded coating or a graded doping within the glass matrix.

The light-blocking member 104 or 106 of FIG. 12B has an aperture 110 that is wedge-shaped and that widens with increasing η so that the light-blocking member blocks more light closer to first end 104a or 106a than at second end 104b or 106b. Aperture 110 has an aperture angle γ that dictates the rate of change of transmittance T(η) and thus the rate of change of the intensity I(x) of input light 62F incident upon prism-sample interface 50 or that reaches photodetector system 130.

Experiments to measure the contrast improvement and standard deviation of the surface compression for doubly-ion-exchanged samples 20, where the first ion exchange was produced in molten $KNO_3$ bath, while the second was produced in a $KNO_3$ bath containing up to 0.6 weight-% $AgNO_3$. Substantial improvement in contrast was obtained using the light-blocking member 104 of FIG. 12B, wherein the first 2 mm to 3 mm of input surface 42 of coupling prism 40 closest to sample 40 were block entirely, and using aperture angles γ of about 30°, 40°, and 50°. Of these, the best performance was observed when the aperture angle γ was about 40°. The optimum rate of change of illumination intensity I(x) may depend on the strength of coupling of the lowest-order modes, which are usually most challenging to measure automatically.

Figure 13A:
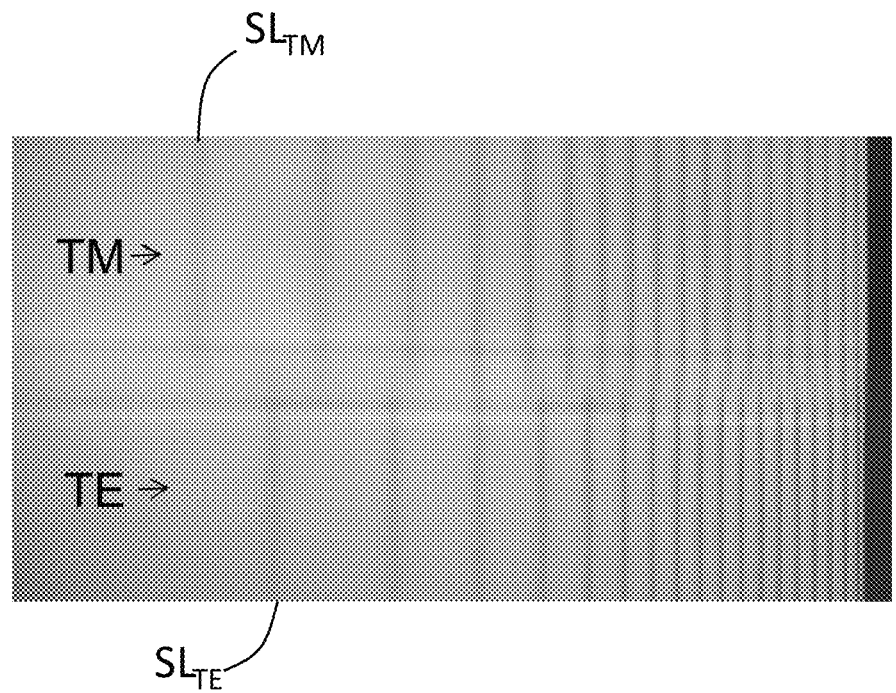
Figure 13B:
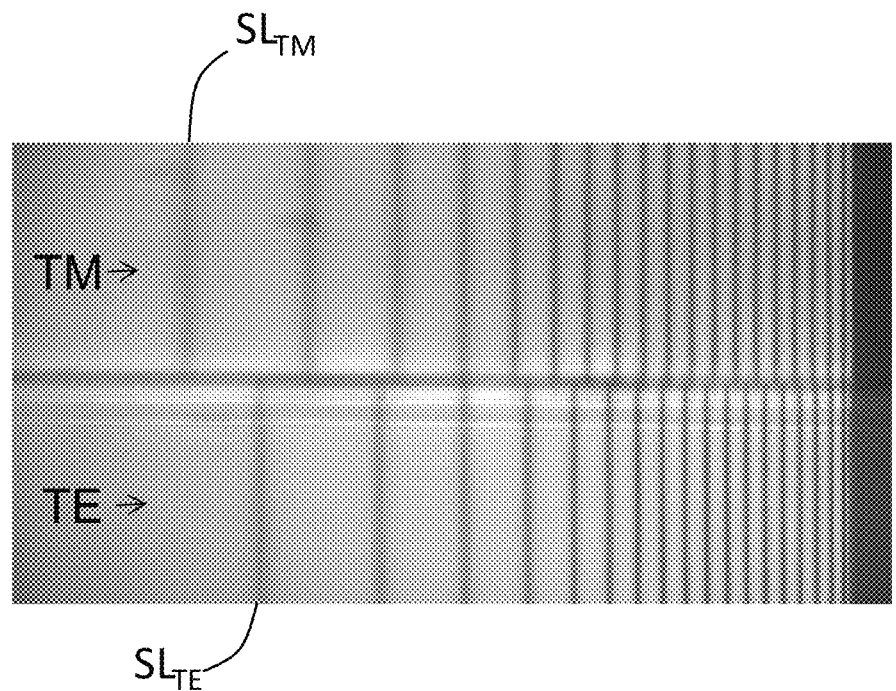

FIGS. 13A and 13B are captured images of TM and TE mode spectra showing TM and TE spectral lines $SL_{TM}$ and $SL_{TE}$. FIG. 13A is a baseline measurement of the TM and TE mode spectra obtained using conventional prism coupling with uniform illumination of the prism-sample interface 50. FIG. 13B shows the TM and TE mode spectra as captured using gradient illumination of the prism-sample interface. It can be seen from FIGS. 13A and 13B that the TM and TE mode spectral lines $SL_{TM}$ and $SL_{TE}$ of FIG. 13B as captured using gradient illumination have more contrast than those captured using conventional uniform illumination. The increased contrast has been shown to reduce the standard deviation of stress-related measurements of DIOX samples 20. It is also noted that while it is advantageous to use interfacing fluid 53 when coupling sample 20 to coupling prism 40, its use is not an absolute requirement to enjoy the benefits of improved mode spectra contrast when using gradient illumination.

It will be apparent to those skilled in the art that various modifications to the preferred embodiments of the disclosure as described herein can be made without departing from the spirit or scope of the disclosure as defined in the appended claims. Thus, the disclosure covers the modifications and variations, provided they come within the scope of the appended claims and the equivalents thereto.

What is claimed is:

1. A method of characterizing a compressive stress of a double ion-exchanged (DIOX) glass sample having a surface and a base refractive index $n_s$, comprising:
   wetting either a coupling surface of a coupling prism of refractive index $n_p$ or the DIOX sample surface with an interfacing fluid having a refractive index $n_f$;
   interfacing the coupling prism to the surface of the DIOX sample to define a prism-sample interface having input and output ends, with the interfacing fluid residing between the coupling prism and the DIOX sample surface, wherein $n_f$ differs from $n_p$ by no more than 0.03, and wherein the sample has a refractive index profile with a region adjacent the surface that satisfies $$0.0004 \le \left| \frac{\lambda}{n} \frac{dn}{dx} \right| \le 0.0013,$$

where λ is a wavelength of measuring light;
   illuminating the prism-sample interface with the measurement light, wherein the measurement light has an intensity gradient that increases in the direction from the input to the output end of the prism-sample interface;
   digitally capturing TE and TM mode spectra reflected from the prism-sample interface; and
   processing the TE and TM mode spectra to determine the compressive stress of the DIOX sample.

2. The method according to claim 1, wherein the intensity gradient of the measurement light is formed by passing the measurement light through a light-blocking member having a graded transmittance.

3. The method according to claim 2, wherein the graded transmittance is defined by a wedge-shaped aperture.

4. The method according to claim 1, wherein the graded transmittance is linearly varying.

5. A method of characterizing a compressive stress of a double ion-exchanged (DIOX) glass sample having a surface and a base refractive index $n_s$, comprising:
   wetting either a coupling surface of a coupling prism of refractive index $n_p$ or the DIOX sample surface with an interfacing fluid having a refractive index $n_f$;
   interfacing the coupling prism to the surface of the DIOX sample to define a prism-sample interface having input and output ends, with the interfacing fluid residing between the coupling prism and the DIOX sample surface, wherein $n_f$ differs from $n_p$ by no more than 0.03, and wherein the sample has a refractive index profile with a region adjacent the surface that satisfies $$0.0004 \le \left| \frac{\lambda}{n} \frac{dn}{dx} \right| \le 0.0013,$$

where λ is a wavelength of measuring light;
   illuminating the prism-sample interface with the measurement light, wherein a portion of the measurement light at the input end of the prism-sample interface is either partially or completely blocked;
   digitally capturing TE and TM mode spectra reflected from the prism-sample interface; and
   processing the TE and TM mode spectra to determine the compressive stress of the DIOX sample.

6. The method of claim 5, wherein the coupling prism has an output surface and further including either partially or completely blocking a portion of the measurement light that exits the output surface.

7. The method of claim 6, wherein the measurement light is passes through a light-blocking member having a graded transmittance.

8. A method of characterizing a compressive stress of a double ion-exchanged (DIOX) glass sample having a surface and a base refractive index $n_s$, comprising:
   wetting either a coupling surface of a coupling prism of refractive index $n_p$ or the DIOX sample surface with an interfacing fluid having a refractive index $n_f$;
   interfacing the coupling prism to the surface of the DIOX sample to define a prism-sample interface, with the interfacing fluid residing between the coupling prism and the DIOX sample surface, wherein $n_f$ differs from $n_p$ by no more than 0.03, and wherein the sample has a refractive index profile with a region adjacent the surface that satisfies $$0.0004 \le \left| \frac{\lambda}{n} \frac{dn}{dx} \right| \le 0.0013,$$

where λ is a wavelength of measuring light;
 directing the measuring light through a first diffuser and then through an input surface of the coupling prism and then through the interfacing fluid into the substrate surface, wherein the first diffuser is spaced apart from the input surface by 4 cm or less;
 digitally capturing TE and TM mode spectra reflected from the prism-sample interface; and
 processing the TE and TM mode spectra to determine the compressive stress of the DIOX sample.

9. The method according to claim 8, further comprising passing the measurement light through a second diffuser disposed upstream of the first diffuser and at a distance of greater than 4 cm from the input surface.

10. A method according to claim 8, wherein $n_p > 1.7$.

11. A method according to claim 10, wherein $n_p = 1.72$ and $n_f$ is in the range $1.7 \le n_f \le 1.8$.

12. A method according to claim 8, wherein $n_f$ meets at least one of the following relationships: $n_f > n_p$; $n_f \ge n_s + 0.17$; and $-0.01 < n_f - n_p < 0.02$.

13. A method according to claim 8, wherein $0.075 \le n_f - n_p \le 0.0125$.

14. The method according to claim 13, wherein $n_f - n_p = 0.01$.

15. A method of capturing improved-contrast mode spectra of a double ion-exchanged (DIOX) glass sample having a surface with a refractive index $n_0$ and a base refractive index $n_s$, comprising:
 wetting either a coupling surface of a coupling prism or the DIOX sample surface with an interfacing fluid having a refractive index $n_f$;
 interfacing the coupling prism of refractive index $n_p$ to the surface of the DIOX sample to define a prism-sample interface, with the interfacing fluid residing between the coupling prism and the DIOX sample surface, wherein $n_f$ differs from $n_p$ by no more than 0.03, and wherein the sample has a refractive index profile with a region adjacent the surface that satisfies $$0.0004 \le \left| \frac{\lambda}{n} \frac{dn}{dx} \right| \le 0.0130,$$

where λ is a wavelength of measuring light;
 directing the measuring light through a first diffuser and through an input surface of the coupling prism and then through the interfacing fluid into the substrate surface to cause the measuring light to reflect from the prism-sample interface, wherein the first diffuser is located within 4 cm of the input surface; and
 capturing the reflected light with a digital detector to digitally capture TE and TM mode spectra having a first contrast that is at least 10% greater than a contrast formed when the same DIOX sample is measured using a conventional method where $n_f$ is greater than the sample surface index $n_0$ by no more than about 0.12.

16. A method according to claim 15, wherein $n_p > 1.7$.

17. A method according to claim 16, wherein $n_p = 1.72$ and $n_f$ is in the range $1.7 \le n_f \le 1.8$.

18. A method according to claim 15, wherein $n_f$ meets at least one of the following relationships: $n_f > n_p$; $n_f \ge n_s + 0.170.075 \le n_f - n_p \le 0.0125$; $n_f - n_p = 0.01$; and $-0.01 < n_f - n_p < 0.02$.

19. The method of claim 15, further comprising processing the TE and TM mode spectra to determine a compressive stress of the DIOX sample.

20. The method according to claim 15, further comprising passing the measurement light through a second diffuser disposed upstream of the first diffuser and at a distance of greater than 4 cm from the input surface.

21. The method according to claim 15, wherein the DIOX glass sample includes in-diffused K+ and Ag+ ions.

\* \* \* \* \*